United States Patent
Xie et al.

(10) Patent No.: US 11,124,780 B2
(45) Date of Patent: Sep. 21, 2021

(54) GENETICALLY ENGINEERED BACTERIUM USED FOR PRODUCING URIDINE WITH HIGH-YIELD

(71) Applicant: Tianjin University of Science and Technology, Tianjin (CN)

(72) Inventors: Xixian Xie, Tianjin (CN); Ning Chen, Tianjin (CN); Heyun Wu, Tianjin (CN); Guoliang Li, Tianjin (CN); Qiang Li, Tianjin (CN); Xiaoguang Fan, Tianjin (CN); Qingyang Xu, Tianjin (CN); Chenglin Zhang, Tianjin (CN); Yanjun Li, Tianjin (CN); Qian Ma, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 0 days.

(21) Appl. No.: 16/409,858

(22) Filed: May 12, 2019

(65) Prior Publication Data
US 2019/0264185 A1   Aug. 29, 2019

Related U.S. Application Data

(63) Continuation of application No. PCT/CN2018/072020, filed on Jan. 10, 2018.

(51) Int. Cl.
*C12N 9/12* (2006.01)
*C12N 1/20* (2006.01)
*C12P 19/28* (2006.01)
*C12N 15/70* (2006.01)
*C12P 19/38* (2006.01)

(52) U.S. Cl.
CPC ............ *C12N 9/1235* (2013.01); *C12N 1/20* (2013.01); *C12N 15/70* (2013.01); *C12P 19/28* (2013.01); *C12P 19/38* (2013.01); *C12Y 207/06001* (2013.01)

(58) Field of Classification Search
None
See application file for complete search history.

(56) References Cited

PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Chica et al. CurrOpin Biotechnol. Aug. 2005;16(4):378-84. (Year: 2005).*
Singh et al. Curr Protein Pept Sci. 2017, 18, 1-11 (Year: 2017).*

* cited by examiner

*Primary Examiner* — Christian L Fronda

(57) ABSTRACT

The present disclosure relates to a genetically engineered strain with high production of uridine and its construction method and application. The strain was constructed as follows: heterologously expressing pyrimidine nucleoside operon sequence pyrBCAKDFE (SEQ ID NO:1) on the genome of *E coli* prompted by strong promoter $P_{trc}$ to reconstruct the pathway of uridine synthesis; overexpressing the autologous prsA gene coding PRPP synthase by integration of another copy of prsA gene promoted by strong promoter $P_{trc}$ on the genome; deficiency of uridine kinase, uridine phosphorylase, ribonucleoside hydrolase, homoserine dehydrogenase I and ornithine carbamoyltransferase. When the bacteria was used for producing uridine, 40-67 g/L uridine could be obtained in a 5 L fermentor after fermentation for 40-70 h using the technical scheme provided by the disclosure with the maximum productivity of 0.15-0.25 g uridine/g glucose and 1.5 g/L/h respectively which is the highest level of fermentative producing uridine reported at present.

2 Claims, 5 Drawing Sheets

Specification includes a Sequence Listing.

(a) (b)

GENETICALLY ENGINEERED BACTERIUM USED FOR PRODUCING URIDINE WITH HIGH-YIELD

TECHNICAL FIELD

The present disclosure relates to the field of genetic engineering, especially relates to a genetically engineered bacteria used for producing uridine with high-yield as well as a construction method and use thereof.

BACKGROUND

Uridine is widely used in food, health care products, cosmetics and pharmaceutical industry. Uridine is used for industrial production of uridine monophosphate, which can not only be used as flavoring and pharmaceutical raw material, but also can be added to milk powder as a food additive to greatly improve the immunity of infants. In addition, uridine has been increasingly used as precursors for antivirus and antitumor drugs in pharmaceutical industry, such as idoxuridine, broxuridine and floxuridine, etc. The great market demand for uridine brings on the urgent need for low-cost and large-scale uridine production.

At present, the production methods of uridine include chemical synthesis, hydrolysis of RNA and microbial fermentation. The method to produce uridine by chemical synthesis is associated with harsh reaction conditions, complicated operation, environmental pollution and high production cost. Hydrolysis of RNA to produce uridine requires a great deal of high quality RNA which are not easy to obtain and high-cost. In contrast, microbial fermentation is a much more efficient, easy to control, cost-effective and environment-friendly approach for large-scale uridine production.

Strains are the key element for fermentation production of uridine. Breeding of uridine producing strains began in the 1960s and *Escherichia coli, Brevibacterium ammoniagenes, Bacillus megatherium* and *Bacillus subtilis* were selected as the starting strains. In particular, *Bacillus subtilis* was the most reported strain to be used for breeding of uridine producing strains. Almost all microbes are able to synthesize uridine 5'-monophosphate (UMP) through de novo pyrimidine biosynthesis and UMP can be further converted to uridine by dephosphorylation. However, long metabolic pathway, complex metabolic regulation and multiple precursors' requirement together result in a great difficulty in accumulation of uridine. Carbamoyl phosphate synthetase (CPSase), which catalyzes the synthesis of carbamoyl phosphate from bicarbonate, glutamine, and two molecules of ATP, is the rate-limiting enzyme and subject to feedback inhibition by UMP. Therefore, relieving the feedback regulation caused by UMP would be significant for improving the uridine production. Traditional strategy to improve the uridine production of microbes is screening resistant strains of UMP structural analogues after random mutagenesis by nitrosoguanidine or ultraviolet treatment. The researchers at Takeda Chemical Industries, Ltd. obtained a mutant of *Bacillus subtilis* with pyrimidine analogue resistance and deficient uridine phosphorylase activity after several rounds of nitroguanidine mutagenesis treatment and this mutant was capable of producing 55 g/L of uridine in the culture broth. However, due to the unavoidable accumulation of side-mutations during strain development, they typically exhibit growth deficiencies, low stress tolerance or by-product formations that limit their production efficiency. The fact that these strains carry up too many mutations makes unraveling the underlying mechanisms of uridine biosynthesis difficult and this complicates further improvements in the titer, productivity and yield of uridine.

Recent developments of rational metabolic engineering strategies have achieved great successes in constructing biosynthetic routes for many valuable bulk commodity chemicals and genetically defined metabolic strategies have gradually taken the place of the conventional random mutagenesis-selection method and become the mainstream. ZHU hui et al have knocked out, modified and overexpressed a number of key genes and operons related to pyrimidine nucleotide biosynthesis to construct the engineered *B. subtilis* strain TD231-1 which could produce 1.48 g/L uridine and YANG shaomei et al. studied several crucial factors influencing the uridine biosynthesis in *Bacillus subtilis*, including mutations of phosphoribosylpyrophosphate (PRPP) synthetase (prs) and CPSase (pyrAA/pyrAB), and overexpression of heterologous 5'-nucleotidase (sdt1). The finally obtained strain *B subtilis* TD246 produced 8.16 g/L uridine by flask fermentation. Although certain uridine producing *Bacillus subtilis* strains have been obtained through genetic engineering now, their uridine production level is too low to match the industrial production requirements.

SUMMARY OF THE INVENTION

The invention provides a genetically engineered bacteria used for producing uridine with high yield as well as its construction method and use which can be applied to the efficient industrial production of uridine.

The technical solution is as follows:

The invention provides a genetically engineered strain with high production of uridine. The strain is constructed as follows: heterologously expressing pyrimidine nucleoside operon sequence pyrBCAKDFE as shown in SEQ ID NO:1 on the genome of *E. coli* prompted by strong promoter $P_{trc}$ to reconstruct the pathway of uridine synthesis; overexpressing the autologous prsA gene coding PRPP synthase by integration of another copy of prsA gene promoted by strong promoter $P_{trc}$ on the genome; deficiency of uridine kinase, uridine phosphorylase, ribonucleoside hydrolase, homoserine dehydrogenase I and ornithine carbamoyltransferase.

The host cell of the genetically engineered bacteria used for producing uridine is *E. coli* W3110 (ATCC 27325).

The pyrimidine nucleoside operon sequence pyrB-CAKDFE is derived from *B. subtilis* A260 (CGMCC No. 11775).

Further technical solutions of the invention are as follows:

The genetically engineered bacterium for the production of uridine was named *E. coli* UR11. The strain is constructed as follows: heterologously expressing pyrimidine nucleoside operon sequence pyrBCAKDFE (sequence shown in a sequence table as SEQ ID NO:1) promoted by strong promoter $P_{trc}$ (sequence shown in a sequence table as SEQ ID NO:2) on the genome of *E coli* W3110 to reconstruct the pathway of uridine synthesis; deficiency of uridine kinase (udk), uridine phosphorylase (udp), ribonucleoside hydrolase (rihA, rihB and rihC) to block uridine degradation pathways; overexpressing the autologous prsA gene coding PRPP synthase by integration of another copy of prsA gene (sequence shown in a sequence table as SEQ ID NO:3) promoted by strong promoter $P_{trc}$ on the genome to enhance the activity of PRPP synthase, aiming to increase the supply of precursor PRPP; deficiency of homoserine dehydrogenase I (thrA) and ornithine carbamoyltransferase (argF) to weaken the metabolism bypass of the precursor aspartic acid and carbamate phosphoric acid respectively.

Another technical scheme of the invention is to provide a construction method of the genetically engineered bacteria used for producing uridine.

In this disclosure, metabolic engineering of E. coli W3110 was implemented by directed chromosomal modifications using the method of CRISPR/Cas9 meditated genome editing, specifically comprising the following steps:

(1) Reconstructing of the uridine synthesis pathway in Escherichia coli: integrating successively the pyrB-CAKDFE operon genes derived from Bacillus subtilis A260 into the yghX locus on genome of Escherichia coli W3110;

(2) Knocking out the udk, udp, rihA, rihB and rihC genes in turn to block uridine degradation pathways;

(3) Constructing a gene fragment $P_{trc}$-prsA through ligating promoter $P_{trc}$ and prsA gene and integrating the fragment into the trpR locus to increase the supply of precursor PRPP;

(4) Knocking out the thrA gene and the argF gene respectively to weaken the metabolism bypass of the precursor aspartic acid and carbamate phosphoric acid.

Another technical scheme of the invention is to provide a use of the genetically engineered bacteria in the production of uridine.

The invention provides a production method of uridine by using the genetically engineered bacteria above mentioned. Details are as follows:

(1) The shake-flask fermentation:

Preparing a seed broth after activating bacteria, and inoculating into a 500 mL flask by a inoculum size of 10-15% (30 mL of final volume) to be cultured at 37° C., 200 rpm, sealed by nine layer of gause. The pH is maintained to be 7.0-7.2 by supplementing NH$_4$OH, and a 60% (m/v) glucose solution is added for maintaining the fermentation. The fermentation period is 24~30 h.

The optimal fermentation medium is composed of glucose 20-40 g/L, (NH$_4$)$_2$SO$_4$ 1-3 g/L, KH$_2$PO$_4$ 1-3 g/L, MgSO$_4$.7H$_2$O 1-2 g/L, yeast extract 0.1-0.3 g/L, corn steep liquor 1-2 mL/L, FeSO$_4$.7H$_2$O 80-100 mg/L, MnSO$_4$.7H$_2$O 80-100 mg/L, and the rest is water, pH7.0-7.2.

The titer of uridine reached 8-12 g/L after 24-30 h fermentation by the shake flask fermentation.

(2) The fermentor fermentation:

Preparing a seed broth after activating bacteria, and inoculating into a fermentor by a inoculum size of 15-20% to be cultured. The temperature was kept constant at 37° C. The pH was kept constant at 7.0. Dissolved oxygen was maintained at 25-35%. When glucose was exhausted, 80% glucose solution was added at an appropriate rate to maintain the glucose concentration below 5 g/L. The fermentation period is 40-70 h.

The optimal fermentation medium is composed of glucose 15-25 g/L, yeast extract 1-5 g/L, tryptone 1-5 g/L, sodium citrate 0.1-1 g/L, KH$_2$PO$_4$ 1-5 g/L, MgSO$_4$.7H$_2$O 0.1-1 g/L, FeSO$_4$.7H$_2$O 80-100 mg/L, MnSO$_4$—H$_2$O 80-100 mg/L, VB$_3$ 0.5-2 mg/L, VB$_3$ 0.5-2 mg/L, VB$_5$ 0.5-2 mg/L, VB$_{12}$ 0.5-2 mg/L, VH 0.5-2 mg/L, threonine 50-200 mg/L, lysine 50-200 mg/L, methionine 50-200 mg/L, glutamine 50-200 mg/L, arginine 50-200 mg/L, 2 drops of defoamer and the rest is water, pH 7.0-7.2.

The titer of uridine reached 40-67 g/L after 40-70 h fermentation in a 5 L bioreactor.

The Beneficial Effects:

Although certain uridine producing Bacillus subtilis strains have been obtained through genetic engineering now, their uridine production level is too low to match the industrial production requirements. Furthermore, the inventors of the disclosure found that several other drawbacks still seriously hamper their use in uridine production. First, the gene editing efficiency of B. subtilis is relatively low, which increases the difficulty to systematically engineer B. subtilis strains. Second, when Bacillus subtilis is used for uridine fermentation, a large amount of organic nitrogen sources especially corn steep liquor needs to be added to the fermentation medium for accumulation of uridine, which is not conducive to the subsequent product separation and purification process.

The strain provided by the invention possesses better growth characteristics, higher productivity of uridine, and more importantly, it is convenient for further character improvement with clear genetic background, simple and efficient gene operation methods.

The uridine producing strain construction method provided by the invention is a targeted and rational strain construction method, which is more efficient, convenient and operable than the traditional mutagenesis method. The uridine fermentation process provided by the invention has higher productivity and it is cheaper and more efficient.

The fermentation process is more conducive to the subsequent separation and purification of uridine due to the simple of fermentation medium composition.

A yield of 40-67 g/L uridine can be produced in a 5 L bioreactor after fermentation for 40-70 h using the technical scheme provided by the invention with the maximum productivity of 1.5 g/(Lxh) and a conversion rate of glucoside of 0.15-0.25 g uridine/g glucose which is the highest level of fermentative producing uridine reported at present.

DETAILED DESCRIPTION

The invention is further described and illustrated in the following specific examples. Unless otherwise specified, the technical means used in the invention are known to the person skilled in the field. In addition, the description is illustrative of the invention and is not to be construed as limiting the invention, and the substance and scope of the invention shall be limited only by the claims. For technical personnel in this field, without deviating from the substance and scope of the invention, any change or alteration of the material composition and dosage in these descriptions shall also fall within the scope of protection of the invention.

Unless otherwise specified, the percent sign "%" referred to in the description means the percentage of quality. The percentage of solution is the mass (g) of solute per 100 mL of solution and the percentage between different liquids refers to their volume ratio of the mixed solution at 25° C.

Example 1 Construction of Strain *E. coli* UR11

1. The Method of Gene Editing

Figure 1:
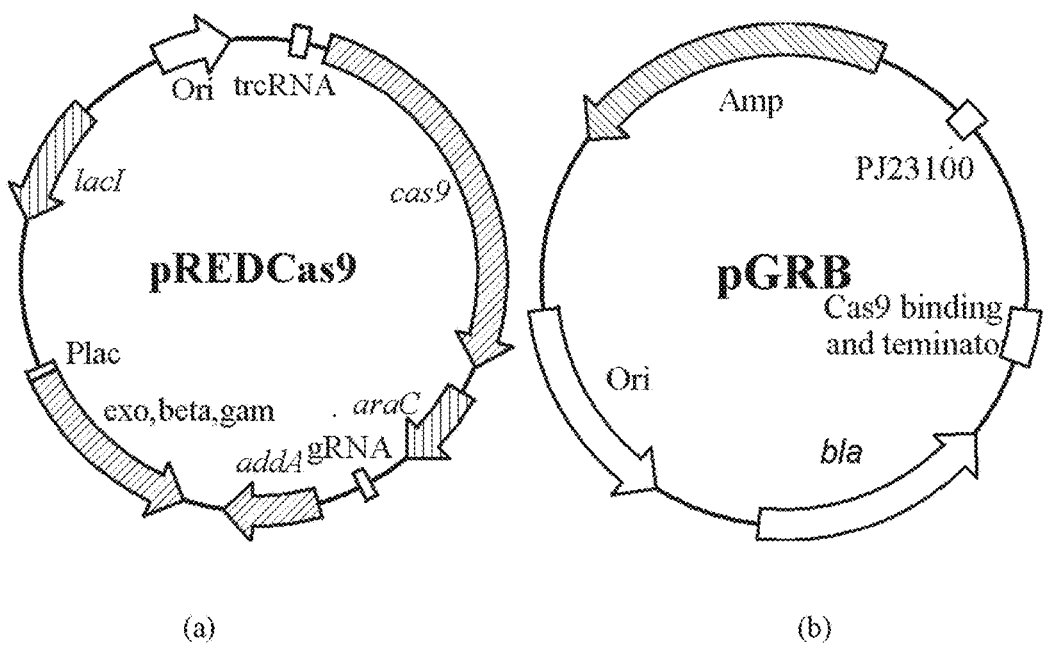
FIG. 1: (a): plasmid profile of pREDCas9; (b): plasmid profile of pGRB.

The gene editing method used in the invention refers to the literature, entitled "metabolic engineering of *Escherichia coli* using CRISPR-Cas9 meditated genome editing", published in the journal of metabolic engineering in 2015 by Li Y, Lin Z, Huang C, et al. Two plasmids, pREDCas9 and pGRB, were used in this method and the plasmid profiles were shown in FIG. 1. pREDCas9 consists of the temperature sensitive pSC101 replication origin, spectinomycin resistance gene, Cas9 expression cassette, IPTG inducibleλ-Red recombination system and L-arabinose inducible $gRNA_{pGRB}$ cassette. pGRB includes the promoter J23100, ampicillin resistance gene, the gRNA scaffold for Cas9 binding and a terminator derived from *S. pyogenes*, and the bla sequence.

The specific steps of this method are as follows:

1.1 Construction of Plasmid pGRB

Plasmid pGRB was constructed to transcribe corresponding gRNA that directs the Cas9 protein to cleave a target DNA sequence with a required protospacer adjacent motif (PAM). To construct the gRNA plasmid, a pair of single stranded DNA (ssDNA) sequences were synthesized and annealed to form the dsDNA that contains the gRNA spacer sequence specific for each target and the flanked sequences homologous to the pGRB backbone. The dsDNA and linearized pGRB were then ligated via homologous recombination.

1.1.1 Design of Target Sequence

Target sequences (PAM:5'-NGG-3') are designed using CRISPR RGEN Tools.

1.1.2 Preparation of DNA Fragments Containing Target Sequences

A pair of single stranded DNA (ssDNA) sequences were synthesized and annealed to form the dsDNA that contains the gRNA spacer sequence specific for each target and the flanked sequences homologous to the pGRB backbone. Annealing conditions: pre-denaturation at 95° C. for 5 min and annealing at 30-50° C. for 1 min. The reaction system is as follows:

| reaction system | Volume (20 µL) |
|---|---|
| single stranded DNA (ssDNA) sequences-S (10 µmol/L) | 10 µL |
| single stranded DNA (ssDNA) sequences-A (10 µmol/L) | 10 µL |

1.1.3 Preparation or Linearized pGRB

The plasmid was linearized by reverse PCR amplification.

1.1.4 Recombination Between the Prepared dsDNA and Linearized pGRB

The dsDNA and linearized pGRB were then ligated via homologous recombination using ClonExpress® II One Step Cloning Kit (Vazyme, China) at 37° C. for 30 min to form the gRNA expressing plasmid. The recombination system is as follows:

| recombination system | Volume (20 μL) |
|---|---|
| 5 × CE II Buffer | 4 μL |
| linearized pGRB | 1 μL |
| DNA fragments containing target sequences | 1 μL |
| Exnase ® II | 2 μL |
| ddH$_2$O | 12 μL |

1.1.5 Plasmid Transformation

10 μL recombinant reaction solution was transformed into 100 μL DH5α competent cells by CaCl$_2$ mediated means and treated by ice bath for 20 min after mixed gently, and then treated by water bath of 42° C. for 45-90 s. After ice bath treatment once again for 2-3 min, cells were immediately added with 0.9 μL SOC and recovered at 37° C. for 1 h. The cells were re-suspend by 200 μL supernate from the centrifugation at 8000 rpm for 2 min and then spreaded onto a plate coated with 100 mg/L penbritin. After overnight culture at 37° C., the single colonies were verified by colony PCR to select the positive recombinants.

1.1.6 Cloning and Identification

The randomly selected positive transformants were then cultured in LB overnight, preserving the strain and extracting the plasmid for identification by restriction enzyme.

1.2 Preparation of DNA Fragment for Recombinant

Recombinant fragment for gene deletion was composed of upstream homologous arm and downstream homologous arm of genes for deletion (upstream homologous arm–downstream homologous arm); recombinant fragment for gene integration was composed of upstream and downstream homologous arm of integration locus and gene fragment for integration (upstream homologous arm—target genes—downstream homologous arm). Using the Primer design software (primer 5), the primers of upstream and downstream homologous arms (400-500 bp) were designed according to the upstream and downstream sequence of the gene to be knocked out or the site to be integrated and the primers of genes to be integrated as the template. The primers of the integrated genes were designed according to the genes to be integrated as the template. The upstream homologous arms, downstream homologous arms and target gene fragment were amplified by PCR and these recombinant fragments were prepared by overlapping PCR. The system and method of PCR are as follows:

PCR System:

| Component | Volume (50 μL) |
|---|---|
| DNA template | 1 μL |
| Upstream Primer (10 μmol/L) | 1 μL |
| Downstream Primer (10 μmol/L) | 1 μL |
| dNTP mixture(10 mmol/L) | 4 μL |
| 5 × Buffer | 10 μL |
| HS enzyme (5 U/μL) | 0.5 μL |
| ddH$_2$O | 32.5 μL |

Overlapping PCR System:

| Component | Volume (50 μL) |
|---|---|
| DNA template | 2 μL |
| Upstream primer of upstream homologous arms (10 μmol/L) | 1 μL |
| Downtream primer of downstream homologous arms (10 μmol/L) | 1 μL |
| dNTP mixture(10 mmol/L) | 4 μL |
| 5 × Buffer | 10 μL |
| HS enzyme (5 U/μL) | 0.5 μL |
| ddH$_2$O | 31.5 μL |

Note: the template was composed of equimolar amplification segments of upstream arm and downstream arm and target gene, and the total amount was less than 10 ng.

Condition of PCR (Takara, PrimeSTAR HS enzyme): denaturation at 95° C. for 5 min; then 30 cycles of denaturation at 98° C. for 10 sec, annealing ((Tm-3/5°) C.) for 15 sec and elongation at 72° C. (this enzyme extended about 1 kb for 1 min); and another elongation at 72° C. for 10 min; finally maintain at 4° C.

1.3 Transformation of the Plasmid and Recombinant DNA

1.3.1 Transformation of pREDCas9

The plasmid pREDCas9 was electrotransformed into *E. coli* W3110 competent cells by electroporation means. The cells were plated on LB agar supplemented with spectinomycin after resuscitation. After overnight culture at 32° C., the single colonies were verified by colony PCR using the designed primer to select the positive recombinants.

1.3.2 Preparation of Electrocompetent Cells Containing pREDCas9

A single colony was cultivated overnight in LB medium at 32° C., and the cultures were transferred into 2×YT medium (1.6% tryptone, 1% yeast extract, 0.5% NaCl) with a 10% inoculum. When the cells grew to an OD of 0.1-0.2 at 32° C., 0.1 mM IPTG was added to induce the expression of λ Red recombinases. The bacteria were harvested to prepare the electrocompetent cells till the OD$_{600}$ reached 0.4-0.5.

1.3.3 Transformation of pGRB and Donor Recombinant Fragment

Eppendorf Eporator (Germany) was used for electroporation (0.1 cm cuvette, 1.80 kV). 200 ng donor DNA and 100 ng gRNA plasmid were added in each electroporation reaction. Cells after electroporation were immediately added into 1 mL LB and recovered at 32° C. for 2 h prior to plating on LB agar supplemented with ampicillin and spectinomycin. After overnight culture at 32° C., the single colonies were verified by colony PCR.

1.4 Curing of Plasmid

1.4.1 Curing of pGRB

For pGRB plasmid curing, the positive recombinants were inoculated in LB liquid medium containing 0.2% L-arabinose and cultivated overnight, and then diluted and spread to LB plating containing spectinomycin and cultivated overnight. The single colonies which grow in the LB plating containing penbritin while cannot grow in the LB plating containing spectinomycin were selected.

1.4.2 Curing of Plasmid pREDCas9

For gRNA plasmid curing, correct colonies were inoculated in LB containing 0.2% L-arabinose and cultivated overnight. The plasmid pREDCas9 could be cured by cultivation at 42° C. for 6-8 h when the strain was not subjected to further engineering.

2. Primers Used in Strain Construction
All primers used in strain construction are as follows:

| Primers | Sequence (5'-3') |
|---|---|
| UP-yghX-S | GCGCAACGTAGAACAGGAATT |
| UP-yghX-A | ATTGTTATCCGCTCACAATTCCACACATTATACGAGCCGGATGATTAATTGTCAAGATTGAAGCGCCTTTACTACTCC |
| pyrB-S | TATAATGTGTGGAATTGTGAGCGGATAACAATTTCACACAAGGAGATATACCATGAAGCATTTAACGACGATGAG |
| pyrB-A | TTACTATGACCAAAAAACCCCTCAAGACCCGTTTAGAGGCCCCAAGGGGTTATGCTAGCCACCTAATTTTTCCTCGGCACTCACCATTTTCGTTTAGTATCCAGC |
| DN-yghX-S1 | GGGTTTTTTGGTCATAGTAATCCAGCAACTCTTGTG |
| DN-yghX-A | GAGCAGGTATTTACGTGAACCG |
| UP-pyrC-pyrAA-S | GCATAGCAGAGTGGCAAGGTC |
| UP-pyrC-pyrAA-A | CCTACAAATTGAGTTATGTTCATGGCTTGTGTTCCCGCATAGT |
| DN-yghX-S2 | ATGAACATAACTCAATTTGTAGGCTAGCATAACCCCTTGG |
| UP-pyrABKDFE-S | CATTACAGCGGAAGAGGTGC |
| UP-pyrABKDFE-A | CCCCAAGGGGTTATGCTAGAGCAAGGCTTTGAAGCCTC |
| DN-yghX-S3 | GAGGCTTCAAAGCCTTGCTCTAGCATAACCCCTTGGGG |
| UP-udp-S | CGCGGATATGTTCATGCAC |
| UP-udp-A | CTGGGTGCGGTTAACGATAGACTTGGACATATACAACTCCTCTG |
| DN-udp-S | CAGAGGAGTTGTATATGTCCAAGTCTATCGTTAACCGCACCCAG |
| DN-udp-A | CATCCGCGTGGTTACTTCA |
| UP-udk-S | AACTGCGAAAGCTCAAGCG |
| UP-udk-A | GCACGATAATGTCCGCATATTGCCAGCGATACCGATAATGACG |
| DN-udk-S | CGTCATTATCGGTATCGCTGGCAATATGCGGACATTATCGTGC |
| DN-udk-A | CTGGGTGAAGATAGAACGCCTC |
| UP-rihA-S | AAACTGCTGGAGCGTGTCG |
| UP-rihA-A | CATTACGGTGGCATTCGGTTTGACCTGGGTCGCAATCTAAC |
| DN-rihA-S | GTTAGATTGCGACCCAGGTCAAACCGAATGCCACCGTAATG |
| DN-rihA-A | CATCTTTAATCGGACGTTGCAG |
| UP-rihB-S | CTTCAATAGCCTGCACCGC |
| UP-rihB-A | GTTTTGATGTAGCCGCGCACCCCGGATCACAATCCAGAATA |
| DN-rihB-S | TATTCTGGATTGTGATCCGGGGTGCGCGGCTACATCAAAAC |
| DN-rihB-A | TGCCGGTAACACCCTGAAAC |
| UP-rihC-S | TGACATCTGCTACGCCACGAC |
| UP-rihC-A | GTTACGACGCCAGAGCCAGCGAGTTCGGGTGCAAAAATC |
| DN-rihC-S | GATTTTTGCACCCGAACTCGCTGGCTCTGGCGTCGTAAC |
| DN-rihC-A | AAGCGAGATGGTTCAGCGTA |
| UP-trpR-S | ATGGCGATTGCTCGTCAG |
| UP-trpR-A | CGCCACAAAGCCATTGAGGTGCGGATCAGTAACGACG |
| prsA-S | CGTCGTTACTGATCCGCACCTCAATGGCTTTGTGGCG |
| prsA-A | CGGGTATTTGTAGGACGGATAAATGGCAGGTGAAGGAGGC |

-continued

| Primers | Sequence (5'-3') |
|---|---|
| DN-trpR-S | GCCTCCTTCACCTGCCATTTATCCGTCCTACAAATACCCG |
| DN-trpR-A | CGCCGTTTACTTCCAGAGG |
| UP-thrA-S | ACGGGCAATATGTCTCTGTGTG |
| UP-thrA-A | GTAACGTCATTGCCCGCACGCTTTCCAGAATATCGGCAAC |
| DN-thrA-S | GTTGCCGATATTCTGGAAAGCGTGCGGGCAATGACGTTAC |
| DN-thrA-A | TTTAATCCCCGGATACGCC |
| UP-argF-S | GTGATATGGATGACGGATGGC |
| UP-argF-A | CCTAGAAGAAATCAACCAGCGCATCAGAAAGTCTCCTGTGCATGGACATTTTATCCTCGCATGG |
| DN-argF-S | TGCGCTGGTTGATTTCTTCTAGGGTCATAGTAATCCAGCAACTTGACGGACGAGGTGTTTGAG |
| DN-argF-A | GAGGCGATACTTGCCGTTCT |
| gRNA-yghX-S | AGTCCTAGGTATAATACTAGTGGTGCCTGACGACCATAAAAGTTTTAGAGCTAGAA |
| gRNA-yghX-A | TTCTAGCTCTAAAACTTTTATGGTCGTCAGGCACCACTAGTATTATACCTAGGACT |
| gRNA-pyr1-S | AGTCCTAGGTATAATACTAGTATGAACATAACTCAATTTGTGTTTTAGAGCTAGAA |
| gRNA-pyr1-A | TTCTAGCTCTAAAACACAAATTGAGTTATGTTCATACTAGTATTATACCTAGGACT |
| gRNA-pyr2-S | AGTCCTAGGTATAATACTAGTAGTGCCGAGGAAAAATTAGGGTTTTAGAGCTAGAA |
| gRNA-pyr2-A | TTCTAGCTCTAAAACCCTAATTTTTCCTCGGCACTACTAGTATTATACCTAGGACT |
| gRNA-thrA-S | AGTCCTAGGTATAATACTAGTCGCCAAAATCACCAACCACCGTTTTAGAGCTAGAA |
| gRNA-thrA-A | TTCTAGCTCTAAAACGGTGGTTGGTGATTTTGGCGACTAGTATTATACCTAGGACT |
| gRNA-udk-S | AGTCCTAGGTATAATACTAGTCGTGAATTGCGTGAGCAAGTGTTTTAGAGCTAGAA |
| gRNA-udk-A | TTCTAGCTCTAAAACACTTGCTCACGCAATTCACGACTAGTATTATACCTAGGACT |
| gRNA-udp-S | AGTCCTAGGTATAATACTAGTCTCACTAAAAACGATTTACAGTTTTAGAGCTAGAA |
| gRNA-udp-A | TTCTAGCTCTAAAACTGTAAATCGTTTTTAGTGAGACTAGTATTATACCTAGGACT |
| gRNA-rihA-S | AGTCCTAGGTATAATACTAGTAAAGCAATTACGTCTTCCGCGTTTTAGAGCTAGAA |
| gRNA-rihA-A | TTCTAGCTCTAAAACGCGGAAGACGTAATTGCTTTACTAGTATTATACCTAGGACT |
| gRNA-rihB-S | AGTCCTAGGTATAATACTAGTAATGATGGCGGCGAAACATCGTTTTAGAGCTAGAA |
| gRNA-rihB-A | TTCTAGCTCTAAAACGATGTTTCGCCGCCATCATTACTAGTATTATACCTAGGACT |
| gRNA-rihC-S | AGTCCTAGGTATAATACTAGTCACCGTCGCGGGTAATGTCTGTTTTAGAGCTAGAA |
| gRNA-rihC-A | TTCTAGCTCTAAAACAGACATTACCCGCGACGGTGACTAGTATTATACCTAGGACT |

| Primers | Sequence (5'-3') |
|---|---|
| gRNA-trpR-S | AGTCCTAGGTATAATACTAGTGATGGCAGAACAGCGTCACCGTTTTAGAGCTAGAA |
| gRNA-trpR-A | AGTCCTAGGTATAATACTAGTGATGGCAGAACAGCGTCACCGTTTTAGAGCTAGAA |
| gRNA-argF-S | AGTCCTAGGTATAATACTAGTCTCAAAGCCGATAAAAAAAAGTTTTAGAGCTAGAA |
| gRNA-argF-A | TTCTAGCTCTAAAACTTTTTTTTATCGGCTTTGAGACTAGTATTATACCTAGGACT |

3. Specific Process for Constructing the Bacteria 3.1 Integrating the Pyrimidine Nucleoside Operon Genes Derived from *Bacillus subtilis* into the yghX Locus on the Genome of W3110

*B. subtilis* A260 was obtained from *B. subtilis* 168 by atmospheric and room temperature plasma (ARTP) mutagenesis coupled with high throughput screening method and this strain has been stored in China General Microbiological Culture Collection Center on Dec. 2, 2015 (address: No. 3, yard I, beichen west road, chaoyang district, Beijing, Institute of Microbiology, Chinese Academy of Sciences, zip code: 100101) with a strain preservation number CGMCC NO. 11775. Sequence analysis of the pyrimidine nucleotide biosynthetic operon of *B. subtilis* A260 showed that three consecutive bases from position 2846 to 2848 of pyrAB gene (code the large subunit of CPSase of *B. subtilis*) were missing resulted in the deletion of the 949$^{th}$ amino acid residues of large subunit of CPSase. It is proven that the mutation E949* on the large subunit of *B. subtilis* CPSase was of importance for the resistance to UMP inhibition and we have applied for patent protection for the relevant research results (Chinese Patent CN105671007A).

In this invention, the pyr operon genes (pyrBCAKDFE, consists of pyrB, pyrC, pyrAA, pyrAB, pyrK, pyrD, pyrF and pyrE genes) derived from *Bacillus subtilis* A260 were successively introduced into the yghX locus on genome of *Escherichia coli* W3110 and promoted by the strong promoter $P_{trc}$ by three rounds of integration and assembly to construction the strain *E. coli* UR3.

3.1.1 Integration of $P_{trc}$-pyrB Fragment

Figure 2:
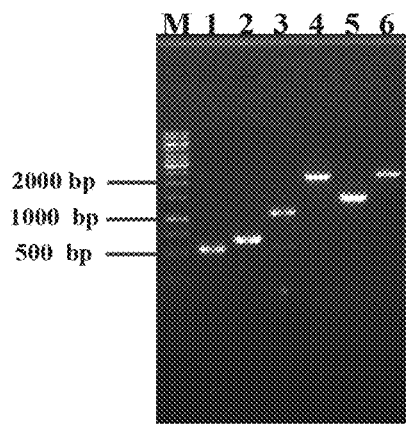
FIG. 2: electrophoretogram for construction and PCR verification of pyrB gene integrated fragment. Wherein, M: 1 kb DNA marker, 1: upstream homologous arm, 2: downstream homologous arm, 3: pyrB fragment, 4: overlapping fragment of upstream homologous arm, pyrB fragment and downstream homologous arm, 5: PCR fragment obtained by using original genomic DNA as template, 6: PCR fragment obtained after replacing yghX gene with pyrB integrated fragment.

The upstream and downstream homologous arms of the yghX gene were amplified by PCR using the genomic DNA of *E. coli* W3110 (ATCC 27325) as a template and the upstream homologous arm primers (UP-yghX-S, UP-yghX-A) and downstream homologous arm primers (DN-yghX-S1, DN-yghX-A) as primers which were designed according to the upstream and downstream sequence of yghX gene; pyrB gene fragment was amplified by PCR using the genomic DNA of *B. subtilis* A260 (CGMCC No. 11775) as a template and pyrB-S and pyrB-A as primers which were designed according to the pyrB gene sequence; sequence of promoter $P_{trc}$ was contained in primers DN-yghX-A and pyrB-S; these fragment were fused together by overlapping PCR generating the pyrB integration fragment (upstream homologous arm-$P_{trc}$-pyrB-downstream homologous arm); the dsDNA to construct the plasmid gRNA-yghX plasmid was obtained by anneal of primer gRNA-yghX-S and primer gRNA-yghX-A. Competent cells of *E. coli* W3110 were prepared and treated following the method shown in chapter 1.3 and 1.4 to construct the strain *E. coli* UR1. Construction and PCR verification of pyrB gene integrated fragment are shown in FIG. 2. Wherein, the upstream homologous arm was 560 bp, the $P_{trc}$-pyrB fragment was 1003 bp, the downstream homologous arm was about 602 bp, all the pyrB integration fragment after fusion was 2239 bp, PCR fragment obtained by PCR amplication after integration of $P_{trc}$-pyrB fragment was 2239 bp, PCR fragment obtained by PCR amplication of the original strain was 1635 bp.

3.1.2 Integration of pyrC-pyrAA Fragment

Figure 3:
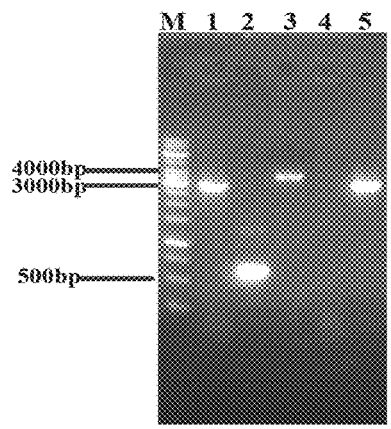
FIG. 3: electrophoretogram for construction and PCR verification of pyrC-pyrAA integrated fragment. Wherein, M: arker, 1: fragment constituted of upstream fragment of pyrC and pyrC-pyrAA fragment, 2: downstream homologous arm, 3: overlapping fragment of upstream fragment of pyrC, pyrC-pyrAA fragment and downstream homologous arm, 4: PCR fragment obtained by using original genomic DNA as template, 5: PCR fragment obtained after integration of pyrC-pyrAA fragment.

The upstream homologous arms (upstream sequence of pyrC-pyrC-pyrAA) was amplified by PCR using the genomic DNA of *B. subtilis* A260 (CGMCC No. 11775) as a template and UP-pyrC-pyrAA-S and UP-pyrC-pyrAA-A as primers which were designed according to upstream sequence of the pyrC gene and the pyrC-pyrAA sequence; the downstream homologous arms of the yghX gene were amplified by PCR using the genomic DNA of *E. coli* UR1 as a template and DN-yghX-S2 and DN-yghX-A as primers which were designed according to the downstream sequence of yghX gene; these two fragment were fused together by overlapping PCR generating the pyrC-pyrAA integration fragment (upstream upstream sequence of the pyrC gene-pyrC-pyrAA-downstream homologous arm); the dsDNA to construct the plasmid gRNA-pyr1 plasmid was obtained by anneal of primer gRNA-pyr1-S and primer gRNA-pyr1-A. Competent cells of *E. coli* UR1 were prepared and treated following the method shown in chapter 1.3 and 1.4 to construct the strain *E. coli* UR2. Construction and PCR verification of pyrC-pyrAA integrated fragment are shown in FIG. 3. Wherein, the upstream homologous arm was 2889 bp, the downstream homologous arm was about 602 bp, all the pyrB integration fragment after fusion was 3468 bp, PCR fragment obtained by PCR amplication after integration of pyrC-pyrAA fragment was 2889 bp and no PCR fragment was obtained by PCR amplication of the original strain.

3.1.3 Integration of pyrAB-pyrK-pyrD-pyrF-pyrE Fragment

Figure 4:
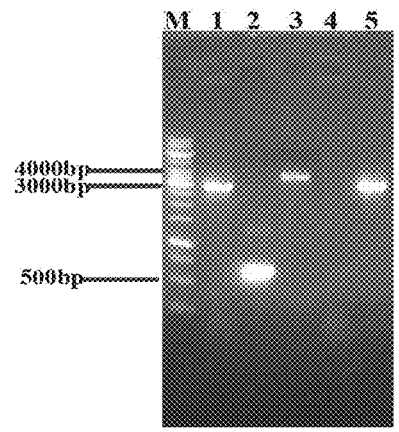
FIG. 4: Construction and PCR verification of pyrAB-pyrK-pyrD-pyrF-pyrE integrated fragment. Wherein, M: Marker, 1: fragment constituted of upstream fragment of pyrAB and pyrAB-pyrK-pyrD-pyrF-pyrE fragment, 2: downstream homologous arm, 3: overlapping fragment of upstream fragment of pyrAB, pyrAB-pyrK-pyrD-pyrF-pyrE fragment and downstream homologous arm, 4: PCR fragment obtained by using original genomic DNA as template, 5: PCR fragment obtained with integration of pyrAB-pyrK-pyrD-pyrF-pyrE fragment.

The upstream homologous arms (upstream sequence of pyrAB-pyrAB-pyrK-pyrD-pyrF-pyrE) was amplified by PCR using the genomic DNA of *B. subtilis* A260 (CGMCC No. 11775) as a template and UP-pyrABKDFE-S and UP-pyrABKDFE-A as primers which were designed according to upstream sequence of the pyrAB gene and the pyrAB-pyrK-pyrD-pyrF-pyrE sequence; the downstream homologous arms of the yghX gene were amplified by PCR using the genomic DNA of *E. coli* UR2 as a template and DN-yghX-S3 and DN-yghX-A as primers which were designed according to the downstream sequence of yghX gene; these two fragment were fused together by overlapping PCR generating the pyrAB-pyrK-pyrD-pyrF-pyrE integration fragment (upstream upstream sequence of the pyrAB gene-pyrAB-pyrK-pyrD-pyrF-pyrE-downstream homologous arm); the dsDNA to construct the plasmid gRNA-pyr2 plasmid was obtained by anneal of primer gRNA-pyr2-S and primer gRNA-pyr2-A. Competent cells of *E. coli* UR2 were prepared and treated following the method shown in chapter 1.3 and 1.4 to construct the strain *E. coli* UR3. Construction and PCR verification of pyrAB-pyrK-pyrD-pyrF-pyrE integrated fragment are shown in FIG. 4. Wherein, the upstream homologous arm was 6757 bp, the downstream homologous arm was about 602 bp, all the pyrB integration fragment after fusion was 7336 bp, PCR fragment obtained by PCR amplication after integration of pyrAB-pyrK-pyrD-pyrF-pyrE fragment was 1262 bp and no PCR fragment was obtained by PCR amplication of the original strain.

Figure 5:
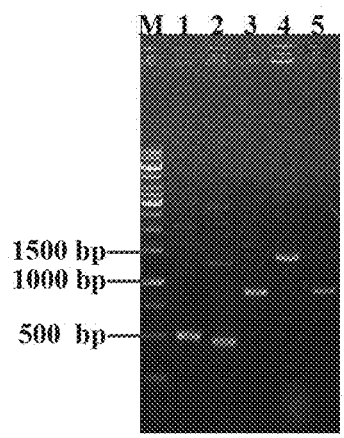
FIG. 5: Deletion and verification of udk gene. Wherein, M: Marker, 1: upstream homologous arm, 2: downstream homologous arm, 3: overlapping fragment of upstream homologous arm and downstream homologous arm, 4: PCR fragment obtained by using original genomic DNA as template, 5: PCR fragment obtained by using genomic DNA with deletion of udk gene as template.

3.2 Knock Out of Genes Related to Uridine Degradation 3.2.1 Deletion of udk Gene The upstream and downstream homologous arms of the udk gene were obtained by PCR amplification using the genomic DNA of *E. coli* W3110 (ATCC27325) as a template and upstream homologous arm primers (UP-udk-S, UP-udk-A) and downstream homologous arm primers (DN-udk-S DN-udk-A) as primers which were designed according to the upstream and downstream sequence of udk gene; these two fragment were fused together by overlapping PCR generating the udk gene deletion fragment. the dsDNA to construct the plasmid gRNA-udk plasmid was obtained by anneal of primer gRNA-udk-S and primer gRNA-udk-A. Competent cells of *E. coli* UR3 were prepared and treated following the method shown in chapter 1.3 and 1.4 to construct the strain *E. coli* UR5. Deletion and verification of udk gene are shown in FIG. 5. Wherein, the upstream homologous arm was 477 bp, the downstream homologous arm was about 436 bp, the udk gene deletion fragment obtained by overlapping PCR was 894 bp; PCR fragment obtained by PCR amplication after deletion of udk gene was 894 bp and PCR fragment by PCR amplication of the original strain was 1422 bp.

3.2.2 Deletion of udp Gene

Figure 6:
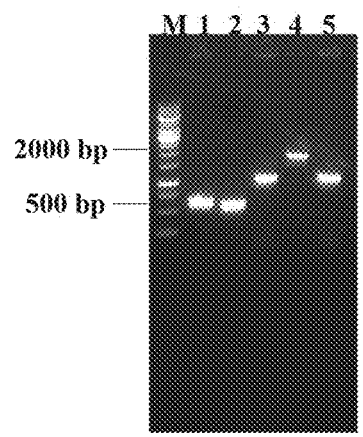
FIG. 6: Deletion and verification of udp gene. Wherein, M: Marker, 1: upstream homologous arm, 2: downstream homologous arm, 3: overlapping fragment of upstream homologous arm and downstream homologous arm, 4: PCR fragment obtained by using original genomic DNA as template, 5 PCR fragment obtained by using genomic DNA with deletion of udp gene as template.

The upstream and downstream homologous arms of the udp gene were obtained by PCR amplification using the genomic DNA of *E. coli* W3110 (ATCC27325) as a template and upstream homologous arm primers (UP-udp-S, UP-udp-A) and downstream homologous arm primers (DN-udp-S DN-udp-A) as primers which were designed according to the upstream and downstream sequence of udp gene; these two fragment were fused together by overlapping PCR generating the udpgene deletion fragment. the dsDNA to construct the plasmid gRNA-udp plasmid was obtained by anneal of primer gRNA-udp-S and primer gRNA-udp-A. Competent cells of *E. coli* UR4 were prepared and treated following the method shown in chapter 1.3 and 1.4 to construct the strain *E. coli* UR5. Deletion and verification of udp gene are shown in FIG. 6. Wherein, the upstream homologous arm was 492 bp, the downstream homologous arm was about 516 bp, the udp gene deletion fragment obtained by overlapping PCR was 1008 bp; PCR fragment obtained by PCR amplication after deletion of udp gene was 1008 bp and PCR fragment by PCR amplication of the original strain was 1653 bp.

3.2.3 Deletion of rihA Gene

Figure 7:
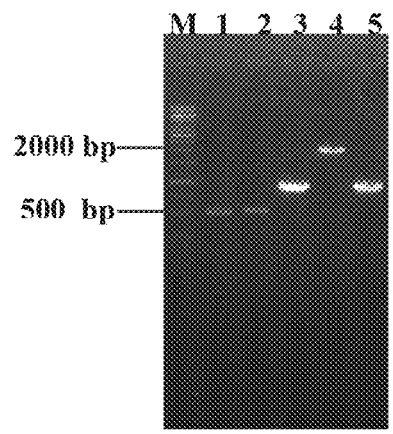
FIG. 7: Deletion and verification of rihA gene. Wherein, M: Marker, 1: upstream homologous arm, 2: downstream homologous arm, 3: overlapping fragment of upstream homologous arm and downstream homologous arm, 4: PCR fragment obtained by using original genomic DNA as template, 5: PCR fragment obtained by using genomic DNA with deletion of rihA gene as template.

The upstream and downstream homologous arms of the rihA gene were obtained by PCR amplification using the genomic DNA of *E. coli* W3110(ATCC27325) as a template and upstream homologous arm primers (UP-rihA-S, UP-rihA-A) and downstream homologous arm primers (DN-rihA-S DN-rihA-A) as primers which were designed according to the upstream and downstream sequence of rihA gene; these two fragment were fused together by overlapping PCR generating the rihA gene deletion fragment. the dsDNA to construct the plasmid gRNA-rihA plasmid was obtained by anneal of primer gRNA-rihA-S and primer gRNA-rihA-A. Competent cells of *E. coli* UR5 were prepared and treated following the method shown in chapter 1.3 and 1.4 to construct the strain *E. coli* UR6. Deletion and verification of rihA gene are shown in FIG. 7. Wherein, the upstream homologous arm was 527 bp, the downstream homologous arm was about 515 bp, the rihA gene deletion fragment obtained by overlapping PCR was 1021 bp; PCR fragment obtained by PCR amplication after deletion of rihA gene was 1021 bp and PCR fragment by PCR amplication of the original strain was 1857 bp.

3.2.4 Deletion of rihB Gene

Figure 8:
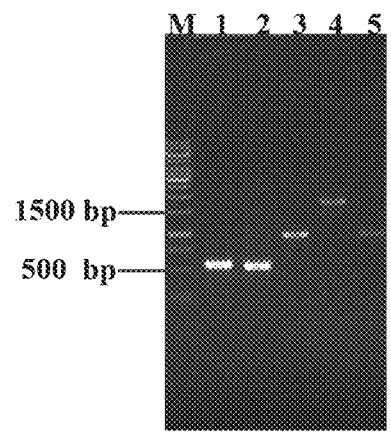
FIG. 8: Deletion and verification of rihB gene. Wherein, M: Marker, 1: upstream homologous arm, 2: downstream homologous arm, 3: overlapping fragment of upstream homologous arm and downstream homologous arm, 4: PCR fragment obtained by using original genomic DNA as template, 5: PCR fragment obtained by using genomic DNA with deletion of rihB gene as template.

The upstream and downstream homologous arms of the rihA gene were obtained by PCR amplification using the genomic DNA of *E. coli* W3110 (ATCC27325) as a template and upstream homologous arm primers (UP-rihB-S. UP-rihB-A) and downstream homologous arm primers (DN-rihB-S, DN-rihB-A) as primers which were designed according to the upstream and downstream sequence of rihB gene; these two fragment were fused together by overlapping PCR generating the rihA gene deletion fragment. the dsDNA to construct the plasmid gRNA-rihB plasmid was obtained by anneal of primer gRNA-rihB-S and primer gRNA-rihB-A. Competent cells of *E. coli* UR6 were prepared and treated following the method shown in chapter 1.3 and 1.4 to construct the strain *E. coli* UR7. Deletion and verification of rihB gene are shown in FIG. 8. Wherein, the upstream homologous arm was 474, the downstream homologous arm was about 438, the rihB gene deletion fragment obtained by overlapping PCR was 891; PCR fragment obtained by PCR amplication after deletion of rihB gene was 891 and PCR fragment by PCR amplication of the original strain was 1789 bp.

3.2.5 Deletion of rihC Gene

Figure 9:
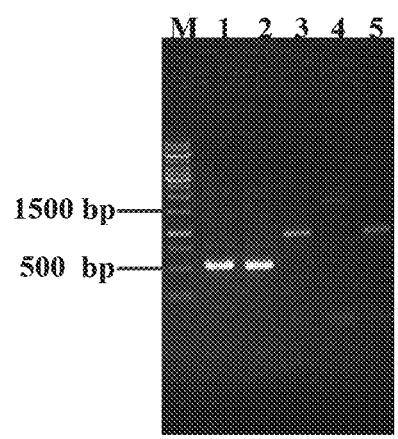
FIG. 9: Deletion and verification of rihC gene. Wherein, M: 1 kb DNA marker, 1: upstream homologous arm, 2: downstream homologous arm, 3: overlapping fragment of upstream homologous arm and downstream homologous arm, 4: PCR fragment obtained by using original genomic DNA as template, 5: PCR fragment obtained by using genomic DNA with deletion of rihC gene as template.

The upstream and downstream homologous arms of the rihC gene were obtained by PCR amplification using the genomic DNA of *E. coli* W3110(ATCC27325) as a template and upstream homologous arm primers (UP-rihC-S. UP-rihC-A) and downstream homologous arm primers (DN-rihC-S DN-rihC-A) as primers which were designed according to the upstream and downstream sequence of rihC gene; these two fragment were fused together by overlapping PCR generating the rihC gene deletion fragment. the dsDNA to construct the plasmid gRNA-rihC plasmid was obtained by anneal of primer gRNA-rihC-S and primer gRNA-rihC-A. Competent cells of *E. coli* UR7 were prepared and treated following the method shown in chapter 1.3 and 1.4 to construct the strain *E. coli* UR8. Deletion and verification of rihC gene are shown in FIG. 9. Wherein, the upstream homologous arm was 520 bp, the downstream homologous arm was about 455, the rihC gene deletion fragment obtained by overlapping PCR was 955; PCR fragment obtained by PCR amplication after deletion of rihC gene was 955 and PCR fragment by PCR amplication of the original strain was 1787 bp.

3.3 Integration of $P_{trc}$-prsA Fragment on trpR Gene Locus

Figure 10:
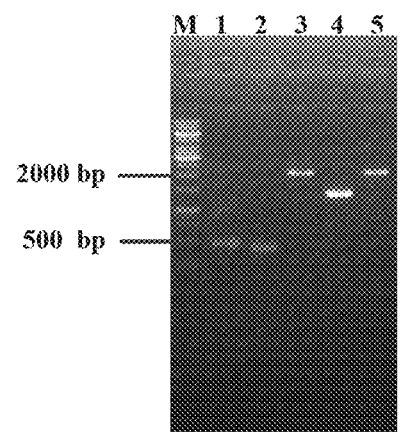
FIG. 10: Construction and PCR verification of $P_{trc}$-prsA integrated fragment. Wherein, M: 1 kb DNA marker, 1: upstream homologous arm, 2: downstream homologous arm, 3: overlapping fragment of upstream homologous arm, $P_{trc}$-prsA fragment and downstream homologous arm, 4: PCR fragment obtained by using original genomic DNA as template, 5: PCR fragment obtained by using genomic DNA with integration of $P_{trc}$-prsA fragment as template.

The upstream and downstream homologous arms of the trpR gene were obtained by PCR amplification using the genomic DNA of *E. coli* W3110 (ATCC27325) as a template and upstream homologous arm primers (UP-trpR-S. UP-trpR-A) and downstream homologous arm primers (DN-trpR-S DN-trpR-A) as primers which were designed according to the upstream and downstream sequence of trpR gene; prsA gene fragment was amplified by PCR using the genomic DNA of *E. coli* W3110(ATCC27325) as a template and prsA-S and prsA-A as primers which were designed according to the prsA gene sequence; sequence of promoter $P_{trc}$ was contained in primers DN-trpR-A and prsA-S; these fragment were fused together by overlapping PCR generating the $P_{trc}$-prsA integration fragment (upstream homologous arm-$P_{trc}$-prsA-downstream homologous arm); the dsDNA to construct the plasmid gRNA-trpR plasmid was obtained by anneal of primer gRNA-trpR-S and primer gRNA-trpR-A. Competent cells of E. coli UR8 were prepared and treated following the method shown in chapter 1.3 and 1.4 to construct the strain E. coli UR9. Construction and PCR verification of $P_{trc}$-prsA gene integrated fragment are shown in FIG. 10. Wherein, the upstream homologous arm was 451 bp, the prsA fragment was 1243 bp, the downstream homologous arm was about 404 bp, all the $P_{trc}$-prsA integration fragment after fusion was 2058 bp, PCR fragment obtained by PCR amplication after integration of $P_{trc}$ prsA fragment was 2058 bp, PCR fragment obtained by PCR amplication of the original strain was 1333 bp.

3.4 Deletion of thrA Gene

Figure 11:
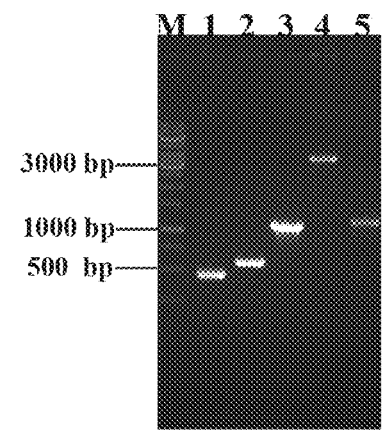
FIG. 11: Deletion and verification of thrA gene. Wherein, M: 1 kb DNA marker, 1: upstream homologous arm, 2: downstream homologous arm, 3: overlapping fragment of upstream homologous arm and downstream homologous arm, 4: PCR fragment obtained by using original genomic DNA as template, 5: PCR fragment obtained by using genomic DNA with deletion of thrA gene as template.

The upstream and downstream homologous arms of the thrA gene were obtained by PCR amplification using the genomic DNA of E. coli W3110(ATCC27325) as a template and upstream homologous arm primers (UP-thrA-S, UP-thrA-A) and downstream homologous arm primers (DN-thrA-S DN-thrA-A) as primers which were designed according to the upstream and downstream sequence of thrA gene; these two fragment were fused together by overlapping PCR generating the thrA gene deletion fragment. the dsDNA to construct the plasmid gRNA-thrA plasmid was obtained by anneal of primer gRNA-thrA-S and primer gRNA-thrA-A. Competent cells of E. coli UR9 were prepared and treated following the method shown in chapter 1.3 and 1.4 to construct the strain E. coli UR10. Deletion and verification of thrA gene are shown in FIG. 11. Wherein, the upstream homologous arm was 394 bp, the downstream homologous arm was about 621, the thrA gene deletion fragment obtained by overlapping PCR was 1015; PCR fragment obtained by PCR amplication after deletion of thrA gene was 1015 and PCR fragment by PCR amplication of the original strain was 3323 bp.

3.5 Deletion of argF Gene

Figure 12:
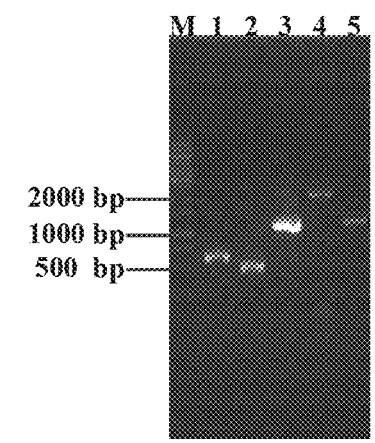
FIG. 12: Deletion and verification of argF gene. Wherein, M: 1 kb DNA marker, 1: upstream homologous arm, 2: downstream homologous arm, 3: overlapping fragment of upstream homologous arm and downstream homologous arm, 4: PCR fragment obtained by using original genomic DNA as template, 5 PCR fragment obtained by using genomic DNA with deletion of argF gene as template.

The upstream and downstream homologous arms of the argF gene were obtained by PCR amplification using the genomic DNA of E. coli W3110(ATCC27325) as a template and upstream homologous arm primers (UP-argF-S. UP-argF-A) and downstream homologous arm primers (DN-argF-S, DN-argF-A) as primers which were designed according to the upstream and downstream sequence of argF gene; these two fragment were fused together by overlapping PCR generating the argF gene deletion fragment. the dsDNA to construct the plasmid gRNA-argF plasmid was obtained by anneal of primer gRNA-argF-S and primer gRNA-argF-A. Competent cells of E. coli UR10 were prepared and treated following the method shown in chapter 1.3 and 1.4 to construct the strain E. coli UR11. Deletion and verification of argF gene are shown in FIG. 12. Wherein, the upstream homologous arm was 568 bp, the downstream homologous arm was about 434, the thrA gene deletion fragment obtained by overlapping PCR was 1002 bp; PCR fragment obtained by PCR amplication after deletion of thrA gene was 1002 and PCR fragment by PCR amplication of the original strain was 1897 bp.

Example 2 Method of Fermentative Producing Uridine by E. coli UR11

(1) Shake-Flask Fermentation

Slant culture: a loop of thallus was scraped off from the strain deposit tube stored in −80° C., and spread evenly on the agar slant culture medium to culture for 12 h, then transferred into a second-generation agar slant to culture for 12 h.

Seed culture: a loop of thallus was inoculated into a 500 mL erlenmeyer flask with 30 mL seed medium, sealed with nine layers of gauze and cultured for 6-8 h at 37° C. and 200 rpm.

Shake-flask fermentation: the seed liquid is inoculated into a fermentation medium according to a inoculum size of 10-15% (a total volume is 30 mL), sealed with nine layers of gauze and cultured for 24-30 h at 37° C. and 200 rpm; The pH is maintained to be 7.0-7.2 by supplementing $NH_4OH$, and a 60% (m/v) glucose solution is added for maintaining the fermentation when needed (the phenol red is used as an indicator, and that the color of the fermentation broth changes no longer means sugar deficiency, and then 1-2 ml of 60% glucose solution is added).

The slant culture medium: glucose 1-5 g/L, tryptone 5-10 g/L, beef extract 5-10 g/L, yeast extract 1-5 g/L, NaCl 1-2.5 g/L, agar 15-20 g/L, the rest is water, pH 7.0-7.2.

The seed medium: glucose 20-30 g/L, $(NH_4)_2SO_4$ 1-5 g/L, $KH_2PO_4$ 1-5 g/L, $MgSO_4.7H_2O$ 1-2 g/L, yeast extract 5-10 g/L, $FeSO_4.7H_2O$ 1-3 mg/L, $MnSO_4$—$H_2O$ 1-3 mg/L, the rest is water, pH 7.0-7.2.

The fermentation medium: glucose 20-40 g/L, $(NH_4)_2SO_4$ 1-3 g/L, $KH_2PO_4$ 1-3 g/L, $MgSO_4.7H_2O$ 1-2 g/L, yeast extract 0.1-0.3 g/L, corn steep liquor 1-2 mL/L, $FeSO_4.7H_2O$ 80-100 mg/L, $MnSO_4.7H_2O$ 80-100 mg/L, the rest is water, pH 7.0-7.2.

The titer of uridine reached 8-12 g/L after 24-30 h fermentation in shake flask.

(2) Bioreactor Fermentation:

Slant culture: a loop of thallus was scraped off from the strain deposit tube stored in −80° C., and spread evenly on the agar slant culture medium to culture for 12-16 h, then transferred into an eggplant bottle to culture for 12-16 h.

Seed culture: transferring the cells cultured in the eggplant bottle into a 5 L bioreactor (Baoxing, Shanghai, China) containing 3 L seed medium. The pH was kept constant at 7.0 by automated addition of $NH_4OH$ (25%, v/v). Dissolved oxygen was maintained above 20% by variation of the stirrer speed and the aeration rate. The temperature was kept constant at 37° C. The seed cultures were continued until $OD_{600}$ of the culture achieved approximately 12-15, and 500 mL of culture broth was retained for the fed-batch cultures.

Bioreactor fermentation: fed-batch cultures were carried out in a 5 L bioreactor containing 3 L medium in total. The pH was kept constant at 7.0 by automated addition of $NH_4OH$ (25%, v/v). Dissolved oxygen was maintained at 25-35% by variation of the stirrer speed and the aeration rate. When glucose was exhausted, 80% glucose solution was added at an appropriate rate to maintain the glucose concentration below 5 g/L. The fermentation period is 40-70 h.

The slant culture or eggplant bottle medium: glucose 1-5 g/L, tryptone 5-10 g/L, beef extract 5-10 g/L, yeast extract 1-5 g/L, NaCl 1-2.5 g/L, agar 15-20 g/L, the rest is water, pH 7.0-7.2.

The seed medium: glucose 15-30 g/L, yeast extract 5-10 g/L, peptone 5-10 g/L, $KH_2PO_4$ 5-15 g/L, $MgSO_4.7H_2O$ 2-5 g/L, $FeSO_4.7H_2O$ 5-15 mg/L, $MnSO_4.H_2O$ 5-15 mg/L, $V_{B1}$ 1-3 mg/L, $V_H$ 0.1-1 mg/L, 2 drops of defoamer and the rest is water, pH 7.0-7.2.

The fermentation medium: glucose 15-25 g/L, yeast extract 1-5 g/L, tryptone 1-5 g/L, sodium citrate 0.1-1 g/L, KH$_2$PO$_4$ 1-5 g/L, MgSO$_4$.7H$_2$O 0.1-1 g/L, FeSO$_4$.7H$_2$O 80-100 mg/L, MnSO$_4$—H$_2$O 80-100 mg/L, VB$_1$ 0.5-2 mg/L, VB$_3$ 0.5-2 mg/L, VB$_5$ 0.5-2 mg/L, VB$_{12}$ 0.5-2 mg/L, VH 0.5-2 mg/L, threonine 50-200 mg/L, lysine 50-200 mg/L, methionine 50-200 mg/L, glutamine 50-200 mg/L, arginine 50-200 mg/L, 2 drops of defoamer and the rest is water, pH 7.0-7.2.

The titer of uridine reached 40-67 g/L after 40-70 h fermentation in a 5 L bioreactor.

Example 3 Fermentation Experiment in a 5 L Bioreactor by *E. coli* UR11

Slant culture: a loop of thallus was scraped off from the strain deposit tube stored in −80° C., and spread evenly on the agar slant culture medium to culture at 37° C. for 12 h, then transferred into an eggplant bottle to culture for 12 h.

Seed culture: transferring the cells cultured in the eggplant bottle into a 5 L bioreactor (Baoxing, Shanghai, China) containing 3 L seed medium. The pH was kept constant at 7.0 by automated addition of NH$_4$OH (25%, v/v). Dissolved oxygen was maintained above 20% by variation of the stirrer speed and the aeration rate. The temperature was kept constant at 37° C. The seed cultures were continued until OD$_{600}$ of the culture achieved approximately 12-15, and 500 mL of culture broth was retained for the fed-batch cultures.

Bioreactor fermentation: fed-batch cultures were carried out in a 5 L bioreactor containing 3 L medium in total. The pH was kept constant at 7.0 by automated addition of NH$_4$OH (25%, v/v). Dissolved oxygen was maintained at 25-35% by variation of the stirrer speed and the aeration rate. When glucose was exhausted, 80% glucose solution was added at an appropriate rate to maintain the glucose concentration below 5 g/L. The fermentation period is 64 h.

The slant medium: glucose 1 g/L, tryptone 10 g/L, beef extract 10 g/L, yeast extract 5 g/L, NaCl 2.5 g/L, agar 25 g/L, the rest is water, pH 7.0.

The seed medium: glucose 25 g/L, yeast extract 5 g/L, tryptone 3 g/L, KH$_2$PO$_4$ 1.2 g/L, MgSO$_4$.7H$_2$O 0.5 g/L, FeSO$_4$.7H$_2$O 10 mg/L, MnSO$_4$—H$_2$O 10 mg/L, V$_{B1}$ 1 mg/L, VB$_3$ 1 mg/L, VB$_5$ 1 mg/L, VB$_{12}$ 1 mg/L, VH 1 mg/L, 2 drops of defoamer and the rest is water, pH 7.0.

The fermentation medium: glucose 20 g/L, yeast extract 4 g/L, tryptone 5 g/L, sodium citrate 2 g/L, KH$_2$PO$_4$ 2 g/L, MgSO$_4$.7H$_2$O 2 g/L, FeSO$_4$.7H$_2$O 20 mg/L, MnSO$_4$.H$_2$O 10 mg/L, VB$_1$ 2 mg/L, VB$_3$ 2 mg/L, VB$_5$ 2 mg/L, VB$_{12}$ 2 mg/L, VH 2 mg/L, threonine 200 mg/L, lysine 200 mg/L, methionine 200 mg/L, glutamine 200 mg/L, arginine 200 mg/L, 2 drops of defoamer and the rest is water, pH 7.0.

Figure 13:
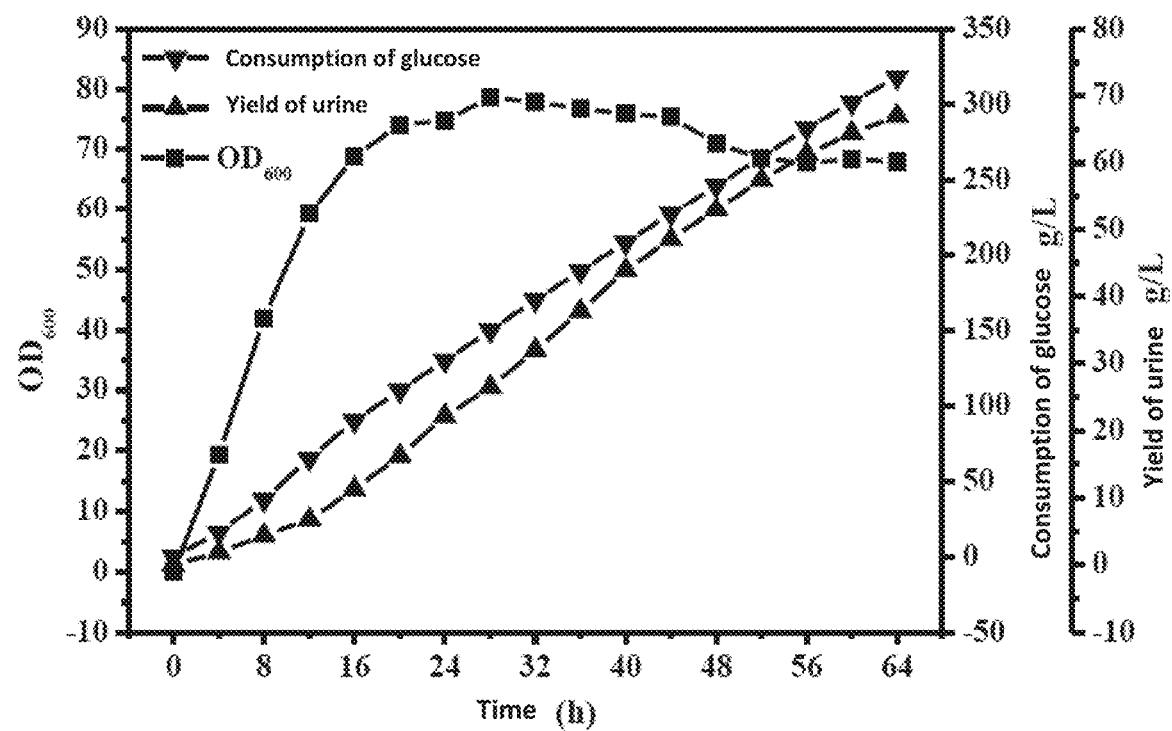
FIG. 13: The fermentation process curve of *E. coli* UR11.

The titer of uridine reached 67 g/L after 64 h fermentation by *E. coli* UR11 in a 5 L bioreactor and the fermentation process curves are shown in FIG. 13.

Although the method of implementation of the invention is better disclosed above, it is not used to limit the invention. Those skilled in the field can make various changes and modifications without breaking away from the spirit and scope of the invention. Therefore, the scope of protection of the invention shall be subject to the limitation of the claim.

What is claimed is:

1. A genetically engineered bacterium used for producing uridine, wherein, the genetically engineered bacterium was constructed as follows: a pyrimidine nucleoside operon sequence pyrBCAKDFE as shown in SEQ ID NO:1 was ligated to a promoter Ptrc with nucleotide sequence of SEQ ID NO: 2 and was integrated on a genome of E. coli W3110 to reconstruct the pathway of uridine synthesis; the autologous prsA gene with nucleotide sequence of SEQ ID NO: 3 coding PRPP (5-phosphoribosyl 1-pyrophosphate) synthase was ligated to a promoter Ptrc with nucleotide sequence of SEQ ID NO:2 and was subject to dual-copy on the genome; and deletion of genes encoding uridine kinase, uridine phosphorylase, ribonucleoside hydrolase, homoserine dehydrogenase I and ornithine carbamoyltransferase comprising udk, udp, rihA, rihB rihC, thrA and argF genes.

2. The genetically engineered bacterium used for producing uridine according to claim 1, wherein, the pyrimidine nucleoside operon sequence pyrBCAKDFE as shown in SEQ ID NO: 1 was ligated to the promoter Ptrc with nucleotide sequence of SEQ ID NO: 2 and was integrated into the yghX locus on the genome of E coli W3110; the udk, udp, rihA, rihB and rihC genes were knocked out; the gene fragment Ptrc-prsA was constructed through ligating the promoter Ptrc with nucleotide sequence of SEQ ID NO:2 and prsA gene with nucleotide sequence of SEQ ID NO: 3 and was integrated into the trpR locus; and the thrA gene was knocked out and the argF gene was knocked out.

* * * * *

SEQUENCE LISTING

```
<160> NUMBER OF SEQ ID NOS: 3

<210> SEQ ID NO 1
<211> LENGTH: 9492
<212> TYPE: DNA
<213> ORGANISM: B. subtilis

<400> SEQUENCE: 1
atgaagcatt taacgacgat gagtgaactt agcactgagg aaatcaaaga tttgcttcaa      60
acagcacaag agctcaaaag cggaaaaaca gacaatcagc ttacaggaaa gtttgcagca     120
aacctgtttt tcgaaccgag cacgagaacg cggttcagct ttgaggtcgc agaaaaaaag     180
ctgggcatga atgtgcttaa ccttgatgga acaagcacaa gcgtgcaaaa aggcgaaacc     240
ttatatgaca cgatccggac gcttgaatca atcggtgtgg acgtctgcgt catcaggcac     300
agtgaggatg agtattatga agagcttgtc agccaggtga acattccgat tctgaatgcg     360
ggagacgggt gcggccagca tccaacacaa tcactgcttg atttaatgac gatttatgaa     420
gagttcaata cgtttaaagg gcttaccgtc tccattcacg gcgacatcaa gcatagcaga     480
gtggcaaggt caaatgcgga agtgttgaca agattgggtg cccgggtcct atttccggc     540 ccttcggaat ggcaggatga agaaaataca ttcggcacgt atgtctcaat ggatgaagca     600
gttgagtctt ccgatgttgt catgctgctg cgcattcaaa atgaacgaca tcagtccgct     660
gtcagtcagg aaggctattt aaacaaatac ggcttgaccg tagaacgggc tgagcgtatg     720
aagcggcatg cgatcatcat gcatcctgct ccggtaaaca gaggagtgga gattgatgac     780
agcttagtag aaagcgaaaa atcaagaatc ttcaagcaaa tgaaaaatgg cgtatttatc     840
agaatggcag tgatacagcg tgccttacaa accaatgtga aaagaggaga agcagcgtat     900
gtcatatctc attaaaaacg gctggatact aaacgaaaat ggtgaaaaaa cacaagcgga     960
```

```
tatccgagtg actggagaaa ccatcaccgc aatcggcaag cttgatgcaa cggataatga    1020
aacggtaatt gatgcaaaag gtttgctcgt ttcacctggg tttgttgatc tccacgtgca    1080
tttcagagag ccgggcggag agaaaaaaga aactattgaa accggggcaa aagcagcggc    1140
gcgcggcggc tatactacag tagcagcaat gccgaatacg cggccggttc ctgatacaaa    1200
ggagcagatg gaatgggtgc aaaacagaat taaagaaaca tcatgcgtaa gagttcttcc    1260
atatgcatcc attacgatca gacaaatcgg cgatgaaatg acaaactttg aagcgttaaa    1320
agaagccggg gcatttgctt ttacagatga cggcgttggt atacagacag caggaatgat    1380
gtatgaagcg atgaaacggg cagccgcaat tgacaaagcg attgttgcac attgcgagga    1440
caactcctta atttacggag ggagcgtaca tgaggggaca ttctccaaag cgaacgggct    1500
aaacggcatt ccttctgtgt gtgaatcggt tcatattgct cgcgatgtgc tgctggctga    1560
ggcggcaaac tgccattatc atgtatgcca tatcagcaca aaagaatctg tcagagttgt    1620
acgcgatgcg aaaaaagcgg gaatcagagt gacagcagaa gtatcgccgc atcatttgct    1680
gctttgtgat gaggacatcc cggggctgga cacaaactat aaaatgaatc ctccgctccg    1740
cagcccagaa gacagagctg ctttaattga aggtctttta gacggaacaa ttgattttat    1800
cgcaacagac catgcaccgc atacggaaga agagaagaac acagaaatga agctggcgcc    1860
attcggaatt gtcggcttag aaacagcatt cccgcttctt tacacacact tgtcaaaaa    1920 tggcagctgg tcactgaagc agctgattga ctacatgaca atcaagccat gcgaagcgtt    1980
cggtctccca tatggaacat acaaacgggg caagctgcg gacattacgt taatcgattt    2040
agaaaaagaa gcagttatag acaaagagac attttatca aaaggaaaaa atacaccatt    2100
caacggcatc agttgcaccg gctggccggt cgctacaatt gcggcaggga agcttgctta    2160
tgaagagggg agacttgtca aatgaagaga cgattagtac tggaaaacgg agcggtattc    2220
gagggagaag ctttcggaag cttagaacac aacatgggag aagtcgtttt taatactggg    2280
atgacaggct atcaggaaat tttatctgat ccttcttact gcggacagat cgtaacatta    2340 acataccccgc ttatcggaaa ttacggcatt aaccgtgatg attttgaatc cattacccct    2400
tttgtcaaag ggctgatcat caaagaatta tgtgagctgc cttccaactg gcgttcagca    2460
tacaccttag acgagtattt aaaaatgaaa acattcccg gactccaggg aattgataca    2520
aggaagctga caagaatgat ccgcacggca ggcgcgctaa aaggaacatt cgcttcatct    2580
gatgaagata tcgaagcagt gctgaaaaga ctgaacgaaa cggaattgcc aagaaatcaa    2640
gtatcccaag tatcagcaaa aacagcatat ccgagcccgg gaagaggcaa acgcattgtc    2700
ttggttgact tcggcatgaa acacgggatt ctaagagagc tgaacaaacg gaaatgtgac    2760
gtcatcgttg tgccttacaa cattacagcg gaagaggtgc ttcagctgaa accgacggt    2820 atcatgcttt ctaacggacc tggagacccg aaggatgtgc ctgaagcgat tgaaatgatt    2880
aaaggtgttc ttggaaaagt gccattattc ggaatatgtc tcggccacca attattcgcg    2940
ctggcgtgcg gggcgaatac tgaaaaaatg aaattcggcc acaggggctc aaaccacccg    3000
gtaaaagagc tggctacagg aaaagttgcc ttaacatctc aaaaccatgg atatacagtt    3060
tcgtctatca gtaaaacaga actggaagtg acgcatatcg caattaacga cgatacgatt    3120
gaagggctga agcataaaac attgccggca tttacggttc aatatcatcc cgaagcctca    3180
cctggtcctg aggatgccaa ccatctattt gacagattca tcgaaatgat cgaaacaaca    3240
gagaaagaag gggaagcggt atgccaaaac gcgtagacat taacaaaatt ttagtaatcg    3300
gatctggacc gatcatcatc ggccaagcag cagaatttga ctatgcggga acacaagcct    3360
```

```
gtcttgcttt gaaagaagaa ggctatgaag tcatccttgt caactcaaac cctgcaacga    3420
tcatgacaga tacagaaatg gctgaccggg tttacatcga accgctcaca cctgaattcc    3480
tgacacgaat catcagaaaa gagcgcccgg atgccattct tcctacactc ggaggccaaa    3540
ccggtttgaa tcttgcggtt gagctttctg aaagaggcgt tttggcagaa tgcggcgtcg    3600
aagtgcttgg cacgaaactg tctgcgattc agcaagctga agaccgtgac ttgttcagaa    3660
cattaatgaa tgaactgaat gaaccggtgc ctgaaagtga gattatccac tcccttgaag    3720
aagcagaaaa attcgtcagt caaattggat tccctgtcat tgtccgcccg gcatatacat    3780
taggcggaac aggcggaggc atctgctcga atgaaacaga gctaaaagaa atcgttgaga    3840
acggcttgaa attaagcccg gtacaccaat gtctgcttga aaaaagcatc gccggctata    3900
aagaaatcga gtatgaagtc atgagagaca gccaggatca cgccattgtc gtttgtaaca    3960
tggaaaacat tgatccagtt ggaatccata ctggagacag tattgttgtc gcgccgagcc    4020
aaacgctcag cgatcgcgaa tatcagctct tgcggaatgt atcgttaaaa ctgattcgcg    4080
cgcttgggat cgaaggcgga tgtaatgtcc agctcgcctt agatccagac agcttccaat    4140
attacattat tgaagtaaat ccgcgtgtca gccgttcatc tgcccttgca tcaaaagcaa    4200
cggggtaccc gattgcaaag ctcgctgcta aaattgcagt cggactttca ttagatgaaa    4260
tgatgaaccc ggtgacagga aaacatatg cagcatttga acctgctctt gactatgtcg    4320
tatccaaaat tccgcgctgg ccgtttgata gtttgaatc agcaaacaga aagcttggca    4380
cgcaaatgaa agcgacaggt gaggtcatgg caatcggccg cacgcttgaa gagtcattgc    4440
tgaaggcagt gcgatcactg gaagcggatg tgtatcatct tgaattgaag gacgccgctg    4500
acatttcaga tgagcttctt gaaaagcgaa ttaaaaaggc cggtgatgaa cgcttattct    4560
acttagctga agcgtacaga agaggctaca cggtagaaga cctccatgaa ttttccgcta    4620
tcgatgtctt cttcttgcat aagctgttcg gaatcgtaca gtttgaaaaa gaattgaagg    4680
ccaatgcggg cgatacagat gtgctgagac gggcaaaaga actcggcttc tctgatcagt    4740
acatcagccg tgaatggaaa atgaaagaat ctgagcttta cagcttgaga aaacaagcgg    4800
ggattgcgcc ggtattcaaa atggtagata catgcgcggc ggaatttgag tcagaaacgc    4860
catacttcta tagcacatat gaagaagaaa atgaatctgt cgttacagat aagaaaagtg    4920
tgatggtgct tggttcgggt ccgattcgaa tcggtcaggg tgtcgagttc gactatgcga    4980
cggttcactc tgtatgggca attaaacaag caggctatga agccattatt gtcaacaaca    5040
acccggaaac cgtttcaaca gacttcagca tctcagacaa gctgtatttt gaaccgctta    5100
cgattgaaga tgtcatgcac atcattgacc tcgaacagcc aatgggcgtt gtcgtacaat    5160
ttggcggaca aactgcgatt aaccttgctg acgagctttc tgcacgcgga gtgaaaatcc    5220
ttggaacttc attagaagat ttagaccgtg ccgaagaccg ggataaattt gaacaagcgc    5280
ttggagaact tggtgttcct cagccgcttg gcaaaacagc gacatcagtt aatcaggcgg    5340
taagcatcgc aagtgatatc ggttatccgg tactggtacg ccccttcctat gtacttggcg    5400 gccgggcgat ggagattgtt taccatgaag aggaactgct tcattacatg aaaaatgcag    5460
tcaaaatcaa tccacagcac cctgtattaa ttgatagata cttgaccgga aaagaaattg    5520
aagtcgatgc agtatccgac ggtgaaacag tcgtcattcc gggaattatg gagcacattg    5580
aacgtgcggg cgttcactcc ggagactcaa tcgctgttta tccgcctcag tctctcacag    5640
aggacattaa gaaaaaaatt gaacaataca cgatcgcatt ggctaagggg ctgaatattg    5700
```

```
tcggtttgct caatattcaa ttcgtcttgt cgcaaggcga ggtgtacgtg ctagaagtga    5760
atccgagatc aagcagaacc gtaccgtttt taagcaaaat tacgggtatc ccaatggcga    5820
atctcgcaac aaaaatcatt cttggtcaaa agctggctgc gtttggctat acagagggcc    5880
ttcagcctga acagcaaggt gtatttgtaa agcgccggt cttctccttt gccaagctga    5940
gaagagtgga tattacgtta gggcctgaaa tgaaatcaac aggtgaagtc atggggaaag    6000
attcgacact tgaaaaggcg ctctacaaag ccttgatcgc ttcaggtatt caaatcccga    6060
actacggttc cgtgctttta acagtagctg ataaggacaa agaagggctt gccattgcta    6120
agcggttcca cgcgatcggc tacaacattt tagcgacgga aggaacggca ggctacctga    6180
aagaagcttc cattccagcg aaggtcgtcg gaaaaatcgg tcaggatggc ccgaacttgc    6240
ttgatgtcat cagaaacgga gaagcgcagt ttgtcatcaa tacgctgaca aaaggaaagc    6300
agccggcaag agacggtttt agaatcagac gtgaatcagt agaaaatggt gttgcctgcc    6360
taacatcttt agatacggca gaggcgtata tgcgagtgct ggaaagcatg acattccgtg    6420
ctgatcaaat gccggcagtc aacacaaatc aggaggcggc agtcactata tgaaaaaagc    6480
gtatttgaca gtatgttcta accagcaaat tgcagaccgg gtgtttcaaa tggttctgaa    6540
aggggagctt gtccaagggt ttacaacccc tggacagttc cttcatctta aagtgagcga    6600
agcggttacg cctcttttga aaggccgat cagcatcgca gacgtcaact ttgaaaaaaa    6660
tgaagtcacc atcatttatc gggtagatgg ggaagggaca agactcttgt cactgaagca    6720
gcagggagaa cttgtggatg tcctcgggcc tttgggaaat ggctttcctg ttaatgaagt    6780
tcaacccgga aagacggctt tgctggtagg aggcggagta ggtgtgccgc ctctccaaga    6840
gctgtcgaaa cgcttgattg aaaaaggggt aaatgtcatc cacgttttag gattccaatc    6900
ggcaaaggat gttttttacg aggaagaatg ccggcagtac ggagacacgt atgtggcaac    6960
agctgacgga agctacgggg aaaccggatt tgtcacagat gtgattaaac ggaaaaagct    7020
agagtttgat atcctcctca gctgcgggcc gacaccgatg ctcaaggcgt taaaacagga    7080
atatgcccat aaagaagtat atctgtccat ggaggaacga atgggctgcg gaatcggcgc    7140
atgcttcgcg tgtgtgtgcc atacaaacga aagtgagaca tcctatgtaa agtatgtct    7200 cgacgggcct gtatttaaag ctcaggaggt ggcgctgtaa tgctagaggt gaaattgccg    7260
ggacttgatt tgaaaaaccc aatcattcct gcatcaggct gcttcggttt tggaaaagaa    7320
ttttcacgtt tttatgattt gtcttgtctt ggagctatca tgattaaggc tacgacaaag    7380
gagccgcgct ttgggaatcc gacgccgcgg gtagctgaga ctggtgctgg aatgctcaat    7440
gcgatcggtc tccaaaatcc ggggctggat agtgtgttgc atcatgagct gccgtggctt    7500
gagcagtttg atacaccgat cattgccaat gtcgcaggtt ctcaagtcga tgattatgtt    7560
gaagtcgcag aacatatcag caaagcgcct aatgttcatg ctcttgaatt gaatatttcc    7620
tgcccgaatg tgaaaacagg cggaatcgct tttggcacga atcctgaaat ggctgccgat    7680
ttgacaaaag cggtgaaaga ggtttcggat gtacccgttt atgtgaagct atccccgaac    7740
gtggctaata tcacagaaat tgcattagcg atcgaggaag cgggagcgga cggtcttacg    7800
atgatcaaca cactaatcgg catgagactc gatttaaaaa ccggcaaacc gatattagcg    7860
aataaaacag ggggactttc gggccctgct gtgaagccgg ttgccattcg catggtgtat    7920
gaagtcagcc agatggtcaa catcccgatt atcggaatgg gaggcgtgca aacggctgaa    7980
gatgccctgg aatttcttct cgcgggagca agcgcagtcg ctgtcggaac agcaaacttt    8040
gtgaatcctt ttgcatgtcc agagattatt gaacagctcc catctgtttt gctccaatac    8100
```

```
ggctatcaat caattgaaga atgcatcgga aggagctgga atcatgaaaa acaacctgcc    8160
catcatcgcg cttgattttg cgtcagctga agaaacactt gcgttcttag cgccttttca    8220
gcaagaaccg ttatttgtaa aggttgggat ggagcttttt tatcaagaag gccatctat     8280 cgtgaaacaa ctaaaagaaa gaaactgcga gctatttta gatctaaagc ttcatgacat     8340
cccgactact gtaaacaaag cgatgaagcg ccttgccagt cttggagtag acctcgtcaa    8400
tgttcatgct gccgggggca aaaaaatgat gcaggcagct ctcgaaggct agaagaagg     8460 tacgccggct ggaaaaaaac gtccgtcact tatcgcggta acccagctga caagcacatc    8520
tgaacaaatc atgaaagatg aactgctgat cgaaaagtct ctgattgata cggttgtgca    8580
ctacagcaaa caggcggaag aaagcggact ggatggagtg gtctgctctg ttcatgaagc    8640
aaaagccatt taccaagcgg tgtcgccttc atttctgact gtcactccgg ggatcagaat    8700
gtcagaggac gctgcgaatg accaagttcg cgtagcgacg cctgccattg caagagagaa    8760
aggttcatca gcgattgtag taggacgctc gattacaaaa gcggaagacc cggtaaaagc    8820
ctataaggct gtcagacttg aatgggaggg aatcaaatct tgaaacaaat catcgcaaaa    8880
catctattag acatccaagc tgtatttta cgcccgaacg agccgttcac atgggcaagc    8940
ggcattttat caccgatcta ctgtgacaac cgccttacgc tatcttccc agaggtcaga    9000 aacgatgttg cttcaggtat cagcaagctt gttaaagagc atttcctga agctgaaatg    9060 attgcgggaa cagcaactgc cggtattcct catgctgctc ttgcggcgga ccatttgaat    9120
cttccgatgt gttatgtgag gagcaagccg aaggcgcacg gaaaggcaa tcagattgag    9180 ggagctgtgc aagaagggca aaaacagtc gtcattgaag acttaatttc cacaggaggc    9240
agcgtgcttg aagcttgtgc agctttacaa gcggccggct gtgaagtgct tggtgtcgtc    9300
tcaatcttta cgtacggact tcctaaagcg gaggaagcct tcgcaaaggc agaactgcca    9360
tactactcat taaccgatta tgatacgctc acagaggtcg cgcttgaaaa cggaaatatt    9420
cattcagatg atctaaaaaa gctgcaaaca tggaaacgaa atcccgagtc aaaagattgg    9480
tttaaaaaat aa                                                        9492

<210> SEQ ID NO 2
<211> LENGTH: 74
<212> TYPE: DNA
<213> ORGANISM: E. coli W3110

<400> SEQUENCE: 2
ttgacaatta atcatccggc tcgtataatg tgtggaattg tgagcggata acaatttcac    60
acaggaaaca gacc                                                      74

<210> SEQ ID NO 3
<211> LENGTH: 948
<212> TYPE: DNA
<213> ORGANISM: E. coli W3110

<400> SEQUENCE: 3
gtgcctgata tgaagctttt tgctggtaac gccaccccgg aactagcaca acgtattgcc    60
aaccgcctgt acacttcact cggcgacgcc gctgtaggtc gctttagcga tggcgaagtc    120
agcgtacaaa ttaatgaaaa tgtacgcggt ggtgatattt tcatcatcca gtccacttgt    180 gccctacta acgacaacct gatgaattag tcgttatgg ttgatgccct gcgtcgtgct    240
tccgcaggtc gtatcaccgc tgttatcccc tactttggct atgcgcgcca ggaccgtcgc    300
```

```
gtccgttccg ctcgtgtacc aatcactgcg aaagtggttg cagacttcct ctccagcgtc    360
ggtgttgacc gtgtgctgac agtggatctg cacgctgaac agattcaggg tttcttcgac    420
gttccggttg ataacgtatt tggtagcccg atcctgctgg aagacatgct gcagctgaat    480
ctggataacc caattgtggt ttctccggac atcggcggcg ttgtgcgtgc ccgcgctatc    540
gctaagctgc tgaacgatac cgatatggca atcatcgaca aacgtcgtcc gcgtgcgaac    600
gtttcacagg tgatgcatat catcggtgac gttgcaggtc gtgactgcgt actggtcgat    660
gatatgatcg acactggcgg tacgctgtgt aaagctgctg aagctctgaa agaacgtggt    720
gctaaacgtg tatttgcgta cgcgactcac ccgatcttct ctggcaacgc ggcgaacaac    780
ctgcgtaact ctgtaattga tgaagtcgtt gtctgcgata ccattccgct gagcgatgaa    840
atcaaatcac tgccgaacgt gcgtactctg accctgtcag gtatgctggc cgaagcgatt    900
cgtcgtatca gcaacgaaga atcgatctct gccatgttcg aacactaa                 948
```